(12) United States Patent
Hinck

(10) Patent No.: US 11,684,958 B2
(45) Date of Patent: Jun. 27, 2023

(54) SYSTEM AND METHOD FOR CLEANING AND SANITIZING FOODSTUFF TANKS

(71) Applicant: Ronald Hinck, San Anselmo, CA (US)

(72) Inventor: Ronald Hinck, San Anselmo, CA (US)

( * ) Notice: Subject to any disclaimer, the term of this patent is extended or adjusted under 35 U.S.C. 154(b) by 531 days.

(21) Appl. No.: 16/776,848

(22) Filed: Jan. 30, 2020

(65) Prior Publication Data

US 2020/0238347 A1 Jul. 30, 2020

Related U.S. Application Data

(60) Provisional application No. 62/798,553, filed on Jan. 30, 2019.

(51) Int. Cl.
| | | |
|---|---|---|
| *A61L 2/00* | (2006.01) |
| *A61L 9/00* | (2006.01) |
| *B08B 3/00* | (2006.01) |
| *B08B 9/00* | (2006.01) |
| *B08B 9/08* | (2006.01) |
| *A61L 2/26* | (2006.01) |
| *A61L 2/22* | (2006.01) |

(52) U.S. Cl.
CPC .............. *B08B 9/0813* (2013.01); *A61L 2/22* (2013.01); *A61L 2/26* (2013.01); *A61L 2202/122* (2013.01); *A61L 2202/15* (2013.01); *A61L 2202/17* (2013.01); *A61L 2202/23* (2013.01); *B08B 2203/007* (2013.01); *B08B 2209/08* (2013.01)

(58) Field of Classification Search
CPC ..... A47L 7/00; A61L 2/00; A61L 2/18; A61L 2/20; A61L 2202/23; B05C 7/00
USPC ...... 422/28, 32, 292, 302; 134/60, 56 R, 26, 134/22.19
See application file for complete search history.

(56) References Cited

U.S. PATENT DOCUMENTS

| | | | |
|---|---|---|---|
| 2004/0020001 A1 | 2/2004 | Lorincz | |
| 2008/0210262 A1* | 9/2008 | Lauzon | B08B 9/08 134/22.12 |
| 2018/0237732 A1 | 8/2018 | Dori | |

* cited by examiner

*Primary Examiner* — Monzer R Chorbaji
(74) *Attorney, Agent, or Firm* — Eandi Fitzpatrick LLP

(57) ABSTRACT

A system and method for cleaning, rinsing, and sanitizing a container is disclosed. The system has a sanitizing agent chamber for storing a sanitizing agent, the one or more solution chambers in fluid communication with the container, a pump in fluid commination with the sanitizing agent, wherein the pump is in communication with a gas, and at least one spray nozzle fluidly connected to the at least one solution chamber via a conduit positioned within the container, wherein the spray nozzle comprises a housing inside which the sanitizing agent is mixed at pressure with the gas to disperse the sanitizing agent and gas mixture into the container for sanitizing the container.

7 Claims, 10 Drawing Sheets

| Treatment Name | Tank# | Tank Capacity (Gallons) | Wine Variety | Tank Site Sampled | Total Microbial Load* | | | | | %CFU Reduction (Post Cleaner) | Log₁₀CFU Reduction (Post Cleaner) | %CFU Reduction (Post Sanitizer) | Log₁₀CFU Reduction (Post Sanitizer) |
|---|---|---|---|---|---|---|---|---|---|---|---|---|---|
| | | | | | Pre-Treatment (CFU) | Pre-Treatment (Log₁₀) | Post Cleaner (CFU) | Post Cleaner (Log₁₀) | Post Sanitizer (CFU) | Post Sanitizer (Log₁₀) | | | | |
| Water Rinse + 270 Xtra + Chlorine Dioxide Spray | 814 | 6,113 | Carbent Sauvignon | Floor | 432 | 2.64 | 86 | 1.93 | 2 | 0.30 | 80.1 | 0.70 | 99.5 | 2.33 |
| | | | | Wall | 306 | 2.49 | 27 | 1.43 | 4 | 0.60 | 91.2 | 1.05 | 98.7 | 1.88 |
| | | | | Ceiling | 192 | 2.28 | 36 | 1.56 | 0 | 0.00 | 81.3 | 0.73 | 100 | 2.28 |
| | | | | Rack Port | 5,700 | 3.76 | 332 | 2.52 | 21 | 1.32 | 94.2 | 1.23 | 99.6 | 2.43 |
| Water Rinse + 270 Xtra + Chlorine Dioxide Spray | 13 | 6,075 | Carbent Sauvignon | Floor | 240 | 2.38 | 13 | 1.11 | 2 | 0.30 | 94.6 | 1.27 | 99.2 | 2.08 |
| | | | | Wall | 137 | 2.14 | 16 | 1.20 | 0 | 0.00 | 88.3 | 0.93 | 100 | 2.14 |
| | | | | Ceiling | 98 | 1.99 | 7 | 0.85 | 0 | 0.00 | 92.9 | 1.15 | 100 | 1.99 |
| | | | | Rack Valve | 1,240 | 3.09 | 32 | 1.51 | 0 | 0.00 | 97.4 | 1.59 | 100 | 3.09 |
| Water Rinse + 270 Xtra + Chlorine Dioxide Spray | 11 | 6,075 | Chardonnay | Floor | 170 | 2.23 | 11 | 1.04 | 1 | 0.00 | 93.5 | 1.19 | 99.4 | 2.23 |
| | | | | Wall | 112 | 2.05 | 18 | 1.26 | 1 | 0.00 | 83.9 | 0.79 | 99.1 | 2.05 |
| | | | | Ceiling | 82 | 1.91 | 29 | 1.46 | 1 | 0.00 | 64.6 | 0.45 | 98.8 | 1.91 |
| | | | | Rack Valve | 18,050 | 4.26 | 37 | 1.57 | 4 | 0.60 | 99.8 | 2.69 | 100 | 3.65 |
| Water Rinse + 270 Xtra + Chlorine Dioxide Rinse | 10 | 6,075 | Sauvignon Blanc | Floor | 321 | 2.51 | 71 | 1.85 | 18 | 1.26 | 77.9 | 0.66 | 94.4 | 1.25 |
| | | | | Wall | 186 | 2.27 | 47 | 1.67 | 12 | 1.08 | 74.7 | 0.60 | 93.5 | 1.19 |
| | | | | Ceiling | 91 | 1.96 | 24 | 1.38 | 13 | 1.11 | 73.6 | 0.58 | 85.7 | 0.85 |
| | | | | Rack Port | 2,850 | 3.45 | 58 | 1.76 | 16 | 1.20 | 98.0 | 1.69 | 99.4 | 2.25 |
| Water Rinse + 270 Xtra + Chlorine Dioxide Rinse | 9 | 6,075 | Merlot | Floor | 192 | 2.28 | 32 | 1.51 | 3 | 0.48 | 83.3 | 0.78 | 98.4 | 1.81 |
| | | | | Wall | 153 | 2.18 | 21 | 1.32 | 10 | 1.00 | 86.3 | 0.86 | 93.5 | 1.18 |
| | | | | Ceiling | 136 | 2.13 | 11 | 1.04 | 3 | 0.48 | 91.9 | 1.09 | 97.8 | 1.66 |
| | | | | Rack Port | 1,760 | 3.25 | 47 | 1.67 | 12 | 1.08 | 97.3 | 1.57 | 99.3 | 2.17 |
| Water Rinse + 270 Xtra + Chlorine Dioxide Rinse | 5 | 6,075 | Chardonnay | Floor | 220 | 2.34 | 18 | 1.26 | 9 | 0.95 | 91.8 | 1.09 | 95.9 | 1.39 |
| | | | | Wall | 302 | 2.48 | 12 | 1.08 | 4 | 0.60 | 96.0 | 1.40 | 98.7 | 1.88 |
| | | | | Ceiling | 128 | 2.11 | 71 | 1.85 | 11 | 1.04 | 44.5 | 0.26 | 91.4 | 1.07 |
| | | | | Rack Valve | 2,200 | 3.34 | 380 | 2.58 | 97 | 1.99 | 82.7 | 0.76 | 95.6 | 1.36 |

| Treatment Name | Sanitizer Volume (Gallons) | Tank# | Tank Capacity (Gallons) | Tank Site Sampled | Total Microbial Load* | | | | | | %CFU Reduction (Post Cleaner) | Log₁₀CFU Reduction (Post Cleaner) | %CFU Reduction (Post Sanitizer) | Log₁₀CFU Reduction (Post Sanitizer) |
|---|---|---|---|---|---|---|---|---|---|---|---|---|---|---|
| | | | | | Pre-Treatment (CFU) | Pre-Treatment (Log₁₀) | Post Cleaner (CFU) | Post Cleaner (Log₁₀) | Post Sanitizer (CFU) | Post Sanitizer (Log₁₀) | | | | |
| 231 Xtra + Citric Acid + Chlorine Dioxide Sprayt | 0.5 | 231 | 6,259 | Floor | 420 | 2.62 | 40 | 1.60 | 3 | 0.48 | 90.5 | 1.02 | 99.3 | 2.15 |
| | | | | Wall | 150 | 2.18 | 14 | 1.15 | 0 | 0.00 | 90.7 | 1.03 | 100 | 2.18 |
| | | | | Ceiling | 618 | 2.79 | 21 | 1.32 | 1 | 0.00 | 96.6 | 1.47 | 99.8 | 2.79 |
| | | | | Rack Valve | 560 | 2.75 | 26 | 1.41 | 3 | 0.48 | 95.4 | 1.33 | 99.5 | 2.27 |
| 231 Xtra + Citric Acid + Chlorine Dioxide Spray | 0.75 | 206 | 9,082 | Floor | 1,260 | 3.10 | 42 | 1.62 | 4 | 0.60 | 96.7 | 1.48 | 99.7 | 2.50 |
| | | | | Wall | 110 | 2.04 | 16 | 1.20 | 5 | 0.70 | 85.5 | 0.84 | 95.5 | 1.34 |
| | | | | Ceiling | 56 | 1.75 | 11 | 1.04 | 5 | 0.70 | 80.4 | 0.71 | 91.1 | 1.05 |
| | | | | Rack Valve | 490 | 2.69 | 123 | 2.09 | 4 | 0.60 | 74.9 | 0.60 | 99.2 | 2.09 |
| 231 Xtra + Citric Acid + Chlorine Dioxide Spray | 1.25 | 209 | 15,091 | Floor | 35,150 | 4.55 | 89 | 1.95 | 4 | 0.60 | 99.7 | 2.60 | 100 | 3.94 |
| | | | | Wall | 22,800 | 4.36 | 28 | 1.45 | 0 | 0.00 | 99.9 | 2.91 | 100 | 4.36 |
| | | | | Ceiling | 42 | 1.62 | 26 | 1.41 | 8 | 0.90 | 38.1 | 0.21 | 81.0 | 0.72 |
| | | | | Rack Valve | 12,350 | 4.09 | 33 | 1.52 | 0 | 0.00 | 99.7 | 2.57 | 100 | 4.09 |
| 231 Xtra + Citric Acid + Peracetic Acid Rinse | 80 | 234 | 6,259 | Floor | 13,300 | 4.12 | 108 | 2.03 | 5 | 0.70 | 99.2 | 2.09 | 100 | 3.42 |
| | | | | Wall | 200 | 2.30 | 15 | 1.18 | 1 | 0.00 | 92.5 | 1.12 | 99.5 | 2.30 |
| | | | | Ceiling | 151 | 2.18 | 18 | 1.26 | 0 | 0.00 | 88.1 | 0.92 | 100 | 2.18 |
| | | | | Rack Valve | 33,250 | 4.52 | 49 | 1.69 | 21 | 1.32 | 99.9 | 2.83 | 99.9 | 3.20 |
| 231 Xtra + Citric Acid + Peracetic Acid Rinse | 80 | 216 | 9,082 | Floor | 290 | 2.46 | 42 | 1.62 | 1 | 0.00 | 85.5 | 0.84 | 99.7 | 2.46 |
| | | | | Wall | 110 | 2.04 | 15 | 1.18 | 4 | 0.60 | 86.4 | 0.87 | 96.4 | 1.44 |
| | | | | Ceiling | 30 | 1.48 | 13 | 1.11 | 3 | 0.48 | 56.7 | 0.36 | 90.0 | 1.00 |
| | | | | Rack Valve | 440 | 2.64 | 35 | 1.54 | 3 | 0.48 | 92.0 | 1.10 | 99.3 | 2.17 |
| 231 Xtra + Citric Acid + Peracetic Acid Rinse | 160 | 214 | 15,091 | Floor | 3,431 | 3.54 | 96 | 1.98 | 1 | 0.00 | 97.2 | 1.55 | 100 | 3.54 |
| | | | | Wall | 220 | 2.34 | 17 | 1.23 | 0 | 0.00 | 92.3 | 1.11 | 100 | 2.34 |
| | | | | Ceiling | 41 | 1.61 | 22 | 1.34 | 9 | 0.95 | 46.3 | 0.27 | 78.0 | 0.66 |
| | | | | Rack Valve | 2,880 | 3.46 | 55 | 1.74 | 0 | 0.00 | 98.1 | 1.72 | 100 | 3.46 |

SYSTEM AND METHOD FOR CLEANING AND SANITIZING FOODSTUFF TANKS

CROSS-REFERENCE TO RELATED APPLICATIONS

This application claims the benefit of U.S. Provisional Application Ser. No. 62/798,553 entitled System and Method for Cleaning and Sanitizing Foodstuff Tanks filed on Jan. 30, 2019, the entire contents of which are incorporated herein by reference for all purposes.

FIELD OF INVENTION

The present invention generally relates to a system and method for cleaning and sanitizing foodstuff tanks. More specifically, the present invention relates to a system and method for wine holding tanks and fermentation tanks, beer tanks, cider, tanks and spirit tanks.

BACKGROUND

Conventional tank cleaning and sanitization is often a long, stringent, hazardous, and labor-intensive task. Conventional methods of tank and vessel cleaning require operator exposure to dangerous environments, use a relatively high volume of harsh or hazardous chemicals, and also, use a high volume of fresh water. To exacerbate the issue, many wine regions are in drought.

An exemplary industry that uses tanks to process contents provided therein is the wine industry. The wine industry uses tanks to receive and process grape juice into wine. The cleanliness of containers holding the juice during processing is arguably one of the most important factors in producing and maintaining wine having the highest character and quality.

Originally, hundreds of years ago, these tanks were made of clay, then wood or concrete, and more recently, from stainless steel. Winemakers utilize these containers in a practically limitless range of sizes and types—with or without jackets for insulation and cooling, with valves and manways and a variety of attachments that permit stirring, punching down, pumping over and removing seeds. In all cases, the tanks needed to be cleaned and sanitized.

At modern wineries, these stainless-steel tanks may be cleaned daily, which requires a massive amount of labor hours, especially considering the elements of the tank that require cleaning, which include but are not limited to the fermenter, airlock, bungs, hoses, siphon and any other pieces of equipment that will come in contact with the wine. Also, wine tanks require cleaning after they are drained, both during crush/fermentation and after they are used for other cellar procedures (wine additions, barrel racking, blending, or bottling).

To evidence the laborious process tank cleaning may be, the following example is provided: Generally, existing tank cleaning (e.g., 6,000 gal) and sanitization procedures utilize steps in which the user fills the stainless-steel sump with 50-100 gallons of warm to hot water and adds 1 to 4 oz. of caustic cleaner, depending on size and soil load, to sump for cleaning. The caustic solution is then circulated using a high-pressure pump and spray-ball for 15 to 30 minutes depending on soil load. Then, the user must empty tank and sump, fill stainless steel sump with another 50-100 gallons of fresh water, circulate the clean water using high pressure pump and a spray-ball for 5 to 10 minutes. Thereafter, the user must empty tank and sump, fill Stainless steel sump with 50-100 gallons of warm water and Citric Acid Solution (if desired to neutralize caustic used in step 1), and circulate water/solution for 5 to 10 minutes using high pressure pump and spray-ball. Then if Citric Acid Solution is used, the previous step is repeated using another 50-100 gallons of clean water which is circulated for 5 to 10 minutes using high-pressure pump and spray-ball.

To then sanitize the tank, a user may empty tank and sump, fill stainless steel sump with 50-100 gallons of PAA or CLO2 solution and circulate using a high-pressure pump and spray-ball for not less than 15 minutes. The tank is then air dried. In this exemplary method, 250 to 500 gallons or fresh water is utilized.

The spray ball referenced above typically includes a nozzle configured to direct a fluid stream to dislodge, dilute, or dissolve settled solids from tank interiors. These systems generally require extensive mounting or setup within the tanks or containers prior to cleaning, during which workers may be subject to prolonged exposures to the contents being cleaned. Additionally, existing tank cleaning systems use fluid directing systems that result in random, wasted movement. For example, some cleaning systems utilize nozzles that perform cleaning via a 360° spherical spray pattern/movement. However, in these systems, cycle of a nozzle cannot be controlled once activated, thereby increasing the difficulty of focusing on specific areas in need of cleaning.

Other systems and methods for cleaning containers include U.S. Pat. No. 4,094,329 to Evans which discloses an apparatus for washing and sanitizing containers in which a conveyor moves containers successively past sprays in treatment zones comprising pre-wash, wash, pre-rinse, primary rinse, and final or secondary rinse zones, between adjacent loading and unloading zones. Freshwater is sprayed in the final rinse zone and collected in a rinse liquid reservoir with liquid sprayed in the primary rinse zone. Used rinse liquid from the rinse liquid reservoir is reused in the primary rinse zone where it is recycled back to the rinse liquid reservoir, after which it is reused still again in both the pre-wash and pre-rinse zones before being drained from the machine. Hot sanitizing caustic solution is recycled between a sanitizing solution reservoir and the wash zone.

U.S. Pat. No. 8,668,779 to Cooper discloses a method of simultaneously cleaning and disinfecting a foodstuff water system. The method involves the addition to the water of the foodstuff water system of a compound selected from the group consisting of the alkali salts of chlorite and chlorate and mixtures thereof; and an acid, followed by allowing the water in the foodstuff water system to circulate for several hours. The reaction of the alkali salts of chlorite and chlorate and acid produces chlorine dioxide in-situ in the water of the foodstuff water system.

However, these past ad hoc approaches are laborious, result in large amounts of wastewater, and utilize high amount of chemicals.

Accordingly, there exists a need an efficient system and method of cleaning and sanitizing foodstuff tanks, such as winery tanks, rapidly with less consumption of water that is also efficient.

SUMMARY OF THE INVENTION

The following summary of the invention is provided in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

To achieve the foregoing and other aspects, a system and method for cleaning tanks or containers such as small to midsize winery tank or a beer tank or barrel, or spirit storage tank, is provided.

Accordingly, the systems provides an efficient and economical method for sanitization and cleaning the container.

Further, the system utilizes far less fresh water and far less sanitization chemicals than known methods and is thus environmentally friendly while still being safe to use and complaint with federal, state and local regulations.

The system and method introduces pressurized gas (e.g., nitrogen) and a sanitizing agent concurrently via a housing in a nozzle which drastically reduces the amount of sanitizing agent and water used in the process previously (80-100 gallons used previously to 0.5 gallons used in this system with like-kind or superior results)

Generally, the system is used for cleaning, rinsing, and sanitizing the container. In one embodiment, the system is configured to enable a user to efficiently clean, rinse, and sanitize the container, for example, a winery tank or a spirit storage tank. In one embodiment, the system comprises at least one or more solution chambers, one or more clean-in-place (CIP) devices, and a spray nozzle. In one embodiment, the solution chambers are used to store one or more liquid solutions, which are used for cleaning, rinsing, and sanitizing the container. In one embodiment, the solution chamber is used to store the liquid solution, for example, a sanitizing agent. In one embodiment, the CIP devices are fluidly connected to one or more solution chambers via at least one or more pumps and multiple conduits. The CIP devices flush the at least one or a mixture of liquid solutions with a high flow rate, thus providing powerful flushing for efficiently cleaning and rinsing the container using at least one or more pumps. In one embodiment, the CIP are spray balls.

In one embodiment, a system and method for cleaning, rinsing, and sanitizing a container is disclosed. The system has a sanitizing agent chamber for storing a sanitizing agent, the one or more solution chambers in fluid communication with the container, a pump in fluid commination with the sanitizing agent, wherein the pump is in communication with a gas, and at least one spray nozzle fluidly connected to the at least one solution chamber via a conduit positioned within the container, wherein the spray nozzle comprises a housing inside which the sanitizing agent is mixed at pressure with the gas to disperse the sanitizing agent and gas mixture into the container for sanitizing the container.

In one embodiment, the system is used for cleaning the container using a cleaning mixture. In one embodiment, the cleaning mixture is prepared by introducing and mixing the liquid solutions, for example, water and a cleaning agent, which are stored in the solution chambers. In one embodiment, the cleaning agent is, but not limited to, a caustic cleaner. In one embodiment, the cleaning mixture is used to clean the container using at least one CIP device, for example, a spray ball. In one embodiment, the system further comprises a heater, which is fluidly connected to the solution chamber. In one embodiment, the solution chamber is used to store at least one liquid solution, for example, water. The heater may heat the liquid solution, for example, water to 160 F to 180 F for efficiently rinsing the container after completion of the cleaning process. The liquid solution from the solution chamber is distributed or circulated within the container using at least one CIP device and at least one pump for efficiently rinsing the container. In one embodiment, the pump is a high-pressure pump.

In one embodiment, the system is used for sanitizing the container using the liquid solution, for example, a sanitizing agent. In one embodiment, the liquid solution is, but not limited to, a sanitizing agent, which is used for a sanitizing process. In one embodiment, the sanitizing agent, chlorine dioxide (ClO2) and peracetic acid (PAA). In one embodiment, at least one spray nozzle is used to facilitate dispersion of the liquid solution, for example, chlorine dioxide (ClO2) and/or peracetic acid (PAA) into a mist/spray for effectively sanitizing the container. In one embodiment, the spray nozzle is fluidly connected to the at least one solution chamber via a line and is securely positioned within the container. The system comprises a nitrogen pump that provides nitrogen that is mixed with the sanitizing agent in a housing at the nozzle concurrently to reduce water use.

In one embodiment, the system uses at least three solution chambers for storing liquid solutions, which are used for efficiently cleaning, rinsing, and sanitizing the container. In one embodiment, the liquid solution includes at least any one or a mixture of water and a cleaning agent, for example, a caustic cleaner, for cleaning the container. In one embodiment, the liquid solution includes at least any one of a sanitizing agent, for example, chlorine dioxide (ClO2) and/or peracetic acid (PAA) for sanitizing the container. In one embodiment, at least one or more pumps is used for circulating the liquid solutions from the solution chambers to the container via one or more conduits.

In one embodiment, a method for cleaning a container is provided. The method comprises connecting the container to a sanitizing agent chamber; pumping a gas at pressure into a housing of a nozzle concurrently with the sanitizing agent; mixing the gas with the sanitizing agent in the housing; pressurizing the gas and sanitizing agent mixture in the housing; and dispersing the sanitizing agent and gas mixture into the container for sanitizing the container.

In one embodiment, at least one CIP device, for example, a spray ball is disposed within the container at a bottom portion and at least one spray nozzle is disposed within the container at a top portion. In one embodiment, the solution chambers are fluidly connected to the CIP device and spray nozzle, respectively via a conduit or a pipeline using a plurality of valves. In one embodiment, a nitrogen pump is securely and operatively connected to the conduit for supplying nitrogen during the sanitizing process to mix the sanitizing agent with nitrogen concurrently. In one embodiment, the rinse liquid is drained out from the container and recovered in a rinse recover using a valve, which is provided at a bottom portion of the container.

In one embodiment, a method is used for cleaning, rinsing, and sanitizing the container using the system. At one step, the container is filled with a liquid solution, for example, hot water from at least anyone of the solution chamber. At another step, the cleaning mixture is prepared by introducing liquid solutions, for example, water and the cleaning agent from the solution chambers, respectively. At another step, the container is cleaned by circulating the cleaning mixture within the container using at least one CIP device, for example, a spray ball, and at least one pump. The container is rinsed by introducing the liquid fluid, for example, water, from the solution chamber using at least one CIP device and at least one pump. In one embodiment, the liquid fluid, for example, water is heated for rinsing process using the heater. The heater is fluidly connected to the solution chamber via a conduit. Further, at another step, the container is sanitized by introducing the liquid solution, for example, a sanitizing agent, within the container using at least one spray nozzle and at least one nitrogen pump. The spray nozzle is configured to facilitate aerated dispersion sanitizing agent. In one embodiment, the sanitizing agent may be chlorine dioxide (ClO2) or peracetic acid (PAA).

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIG. 9 illustrates a table displaying test results and comparative efficacy study of chlorine dioxide/nitrogen spray versus chlorine dioxide rinse in one embodiment of the present invention.

FIG. 10 illustrates a table displaying test results and comparative efficacy study of chlorine dioxide mist versus peracetic acid rinse on interior surfaces of stainless-steel tanks in one embodiment of the present invention.

Figure 1:
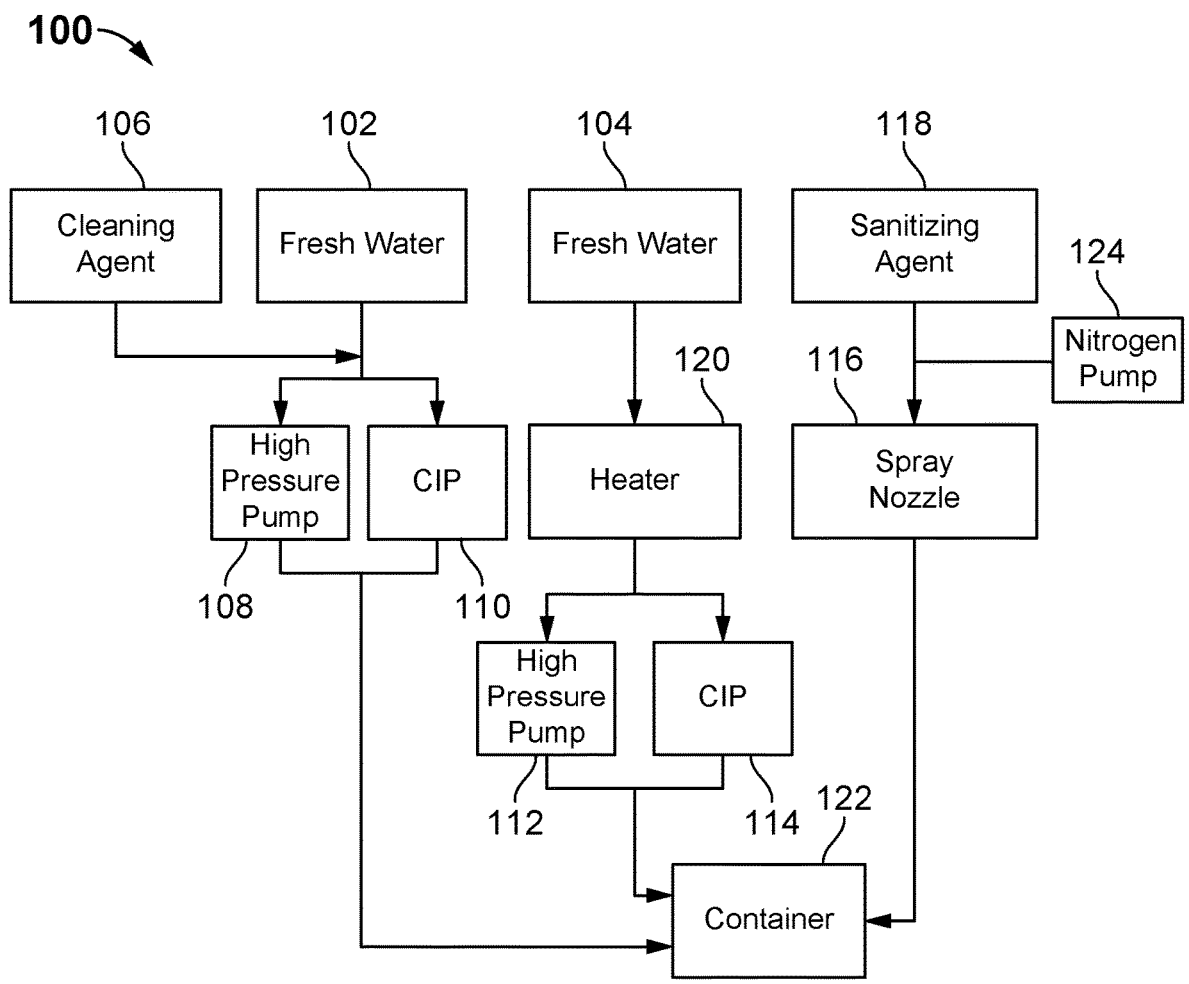
FIG. 1 illustrates a block diagram of a system for cleaning, rinsing, and sanitizing a container in an embodiment of the present invention.

Other features, advantages, and aspects of the present invention will become more apparent and be more readily understood from the following detailed description, which should be read in conjunction with the accompanying drawings.

DETAILED DESCRIPTION OF THE PRESENT INVENTION

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described are shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be also understood to refer to functional equivalents of such structures. The present invention will now be described in detail with reference to embodiments thereof as illustrated in the accompanying drawings.

Specific configurations and arrangements of the invention, discussed above with reference to the accompanying drawing, are for illustrative purposes only. Other configurations and arrangements that are within the purview of a skilled artisan can be made, used, or sold without departing from the spirit and scope of the invention. For example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures.

While the present invention has been described in connection with what are presently considered to be the most practical and preferred embodiments, it is to be understood that the present invention is not limited to these herein disclosed embodiments. Rather, the present invention is intended to include the various modifications and equivalent arrangements included within the spirit and scope of the appended claims.

As used herein, "cleaning" may refer to the overarching system which cleans, rinses, and sanitizes the tank.

As used herein, cleaning agents and sanitizing agents may comprise alkaline or acid base such as Caustic Soda or Soda Ash, Citric Acid, Peroxyacetic Acid, Peroxycarb (more commonly for cleaning barrels affected with Brettanomyces), Chlorine Dioxide, Peracetic Acid, or other substances that may be used to safely clean containers and tanks known now or in the future.

As used herein, a "clean in place (CIP)" device may be a spray ball or other types of devices that are used to clean containers, generally.

As used herein, the term "liquid solution" may refer generally to water or a solution containing water other chemicals.

The systems and methods referred to herein may be utilized and installed "on-site" in a permanent manner but may also be utilized as a mobile system in which an operator is able to bring to a site as a kit, connect the system, run the system and method, and disconnect the system to bring to the next site.

Referring now to FIG. 1, a block diagram of a system 100 for cleaning, rinsing, and sanitizing a container 122 is shown generally at reference numeral 100. In one embodiment, the system 100 is configured to enable a user to efficiently clean, rinse, and sanitize the container 122, for example, a winery tank or a spirit storage tank. In one embodiment, the system 100 comprises at least one or more solution chambers (102, 104, 106, and 118), one or more clean-in-place (CIP) devices (110 and 114), and a spray nozzle 116. The spray nozzle 116 comprises a housing that mixes pressurized nitrogen with the sanitizing agent at pressure (e.g., 10-60 PSI) and has small output holes so that the mixture is dispersed in a fine spray.

In one embodiment, the solution chambers (102, 104, 106, and 118) are used to store one or more liquid solutions, which are used for cleaning, rinsing, and sanitizing the container 122. The solution chamber 118 is used to store the liquid solution, for example, a sanitizing agent. In one embodiment, the CIP devices (110 or 114) are fluidly connected to one or more solution chambers (102, 104, and 106) via at least one or more pumps (108 and 112) and multiple conduits. The CIP devices (110 and 114) are configured to flush the at least one or a mixture of liquid solutions with a high flow rate, thus providing powerful flushing for efficiently cleaning and rinsing the container 122 using at least one or more pumps (108 and 112).

In one embodiment, the system 100 is used first for cleaning the container 122 using a cleaning mixture. In one embodiment, the cleaning mixture is prepared by introducing and mixing the liquid solutions, for example, water and a cleaning agent (e.g., caustic cleaner), which are stored in the solution chambers (102 and 106). The cleaning mixture is used to clean the container 122 using at least one CIP device, for example, a spray ball 110.

The system 100 further comprises a heater 120 which is fluidly connected to the solution chamber 104. In one embodiment, the solution chamber 104 is used to store at least one liquid solution, for example, water. The heater 120 heats the liquid solution, for example, water to a temperature ranging from about 160° F. to about 180° F. for efficiently rinsing the container 122 after completion of the cleaning process. The liquid solution from the solution chamber 104 is distributed or circulated within the container 122 using at least one CIP device 114 and at least one pump 112 for efficiently rinsing the container 122.

After the cleaning process, a rinsing step occurs. In the rinsing step, water is introduced to rinse the cleaning agent from the container. In one embodiment, the rinse liquid is drained out from the container 122 and recovered in a rinse recover using a valve 208, which is provided at a bottom portion of the container 122.

Sanitizing the container 122 using the liquid solution, for example, a sanitizing agent. In one embodiment, the liquid solution is, but not limited to, a sanitizing agent, which is used for a sanitizing process. In one embodiment, the sanitizing agent may be chlorine dioxide ($ClO_2$) or peracetic acid (PAA). The spray nozzle 116 is used to facilitate dispersion of the liquid solution, for example, chlorine dioxide ($ClO_2$) and/or peracetic acid (PAA) to disperse the agent into the tank for effectively sanitizing the container 122. In one embodiment, the spray nozzle 116 is fluidly connected to the at least one solution chamber 118 via a line and is securely positioned within the container 122. The spray nozzle 116 is in communication with a nitrogen pump 124 that introduces nitrogen to the sanitizing agent concurrently in the nozzle 116. In other embodiments, purified or medical grade air could be used in place of nitrogen.

Importantly, this introduction of nitrogen allows the user to use approximately 85-95% less sanitizing agent that in previous systems. Further, by using the system, water use is reduced from approximately 150 gallons to 0.5 gallons for a 6000 gallon tank because the large water rinse step after sanitization is no longer required. The sanitization agent and nitrogen mx will evaporate such that the tank is sanitized and usable 15-20 minutes after the sanitization step for example.

Figure 2:
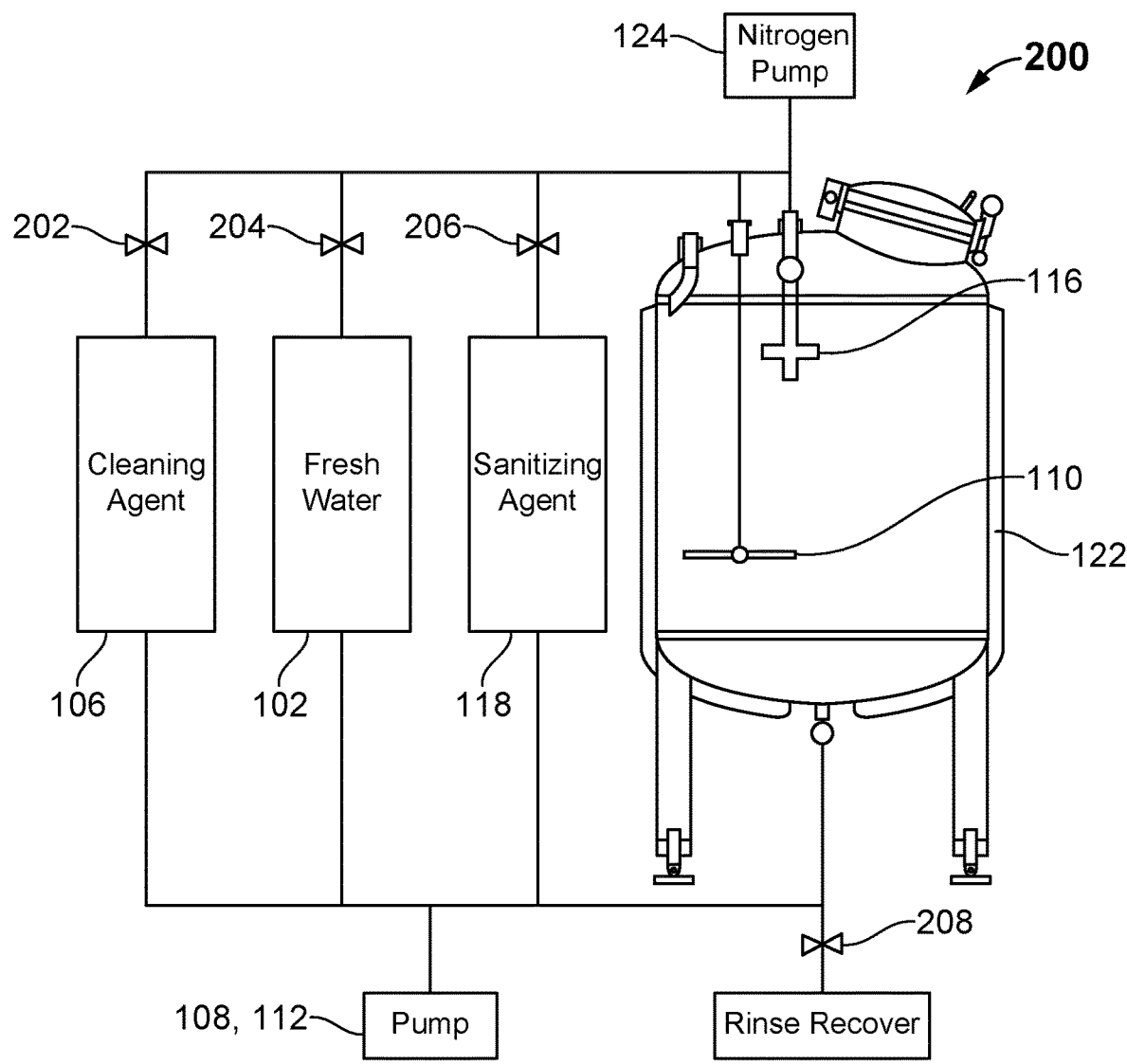
FIG. 2 illustrates an arrangement for cleaning, rinsing, and sanitizing the container using the system in one embodiment of the present invention.

Referring to FIG. 2, an arrangement 200 for cleaning, rinsing, and sanitizing the container 122, for example, a winery tank in one embodiment is disclosed. In one embodiment, the system 100 uses at least three solution chambers (102, 106, and 118) for storing liquid solutions which are used for efficiently cleaning, rinsing, and sanitizing the container 122. In one embodiment, the liquid solution includes at least any one or a mixture of water and a cleaning agent, for example, a caustic cleaner in chamber 106 for cleaning the container 122. In one embodiment, the liquid solution includes at least any one of a sanitizing agent, for example, chlorine dioxide ($ClO_2$) and/or peracetic acid (PAA) in chamber 118 for sanitizing the container 122. In one embodiment, at least one or more pumps (108 and 112) is used for circulating the liquid solutions from the solution chambers (102, 106, and 118) to the container 122 via one or more conduits and also for introducing nitrogen to the spray nozzle concurrently with the sanitizing agent to molecularly disperse the sanitizing agent.

As shown, the CIP device 110, for example, a spray ball, is disposed within the container 122 at a bottom portion and at least one spray nozzle 116 is disposed within the container 122 at a top portion. It should be noted that the either the CIP and/or spray nozzle may be positioned in any portion of the tanks. The solution chambers (102, 106, and 118) are fluidly connected to the CIP device 110 and spray nozzle 116, respectively via a conduit or a pipeline using a plurality of valves (202, 204, and 206). In one embodiment, a nitrogen pump 124 is securely and operatively connected to the conduit for supplying nitrogen to the nozzle during the sanitizing process. The rinse liquid and any waste is drained out from the container 122 and recovered in a rinse recover using a valve 208, which is provided at a bottom portion of the container 122.

Figure 3:
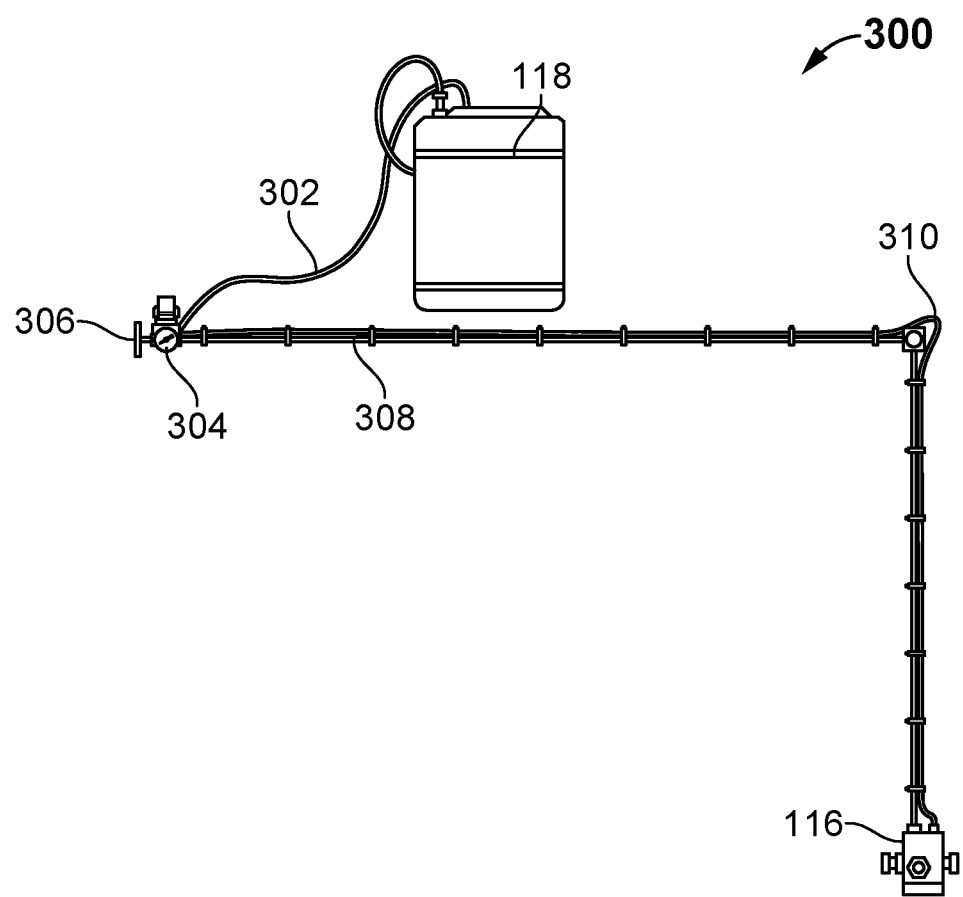
FIG. 3 illustrates a solution chamber used for storing a liquid solution, for example, a sanitizing agent in one embodiment of the present invention.

Referring now to FIG. 3, a solution chamber 118 used to store a sanitizing agent or chemical solution for sanitizing the container is disclosed. In one embodiment, the sanitizing agent is peracetic acid (PAA). The spray nozzle 116 is in communication with the sanitizing agent in the solution chamber 118 via one or more sanitization feed hoses. The sanitization feed hoses comprise a sanitization feed hose feed upper end 302 and a sanitization feed hose feed lower end 310. The sanitization feed hose feed upper end 302 connects the solution chamber 118 to a pressure gauge 304 to effectively measure the pressure of the nitrogen and sanitization agent mixture. The sanitization feed hose feed lower end 310 connects the pressure gauge 304 and the spray nozzle 116. In one embodiment, the pressure gauge 304 comprises a volume controller 306 and an nitrogen tube feed conduit 308. The volume controller 306 is configured to control the amount of inlet nitrogen passing through the nitrogen tube feed conduit 308. In one embodiment, one end of the nitrogen tube feed conduit 308 is connected to the pressure gauge 304, whereas the other end is connected to the spray nozzle 116.

Figure 4:
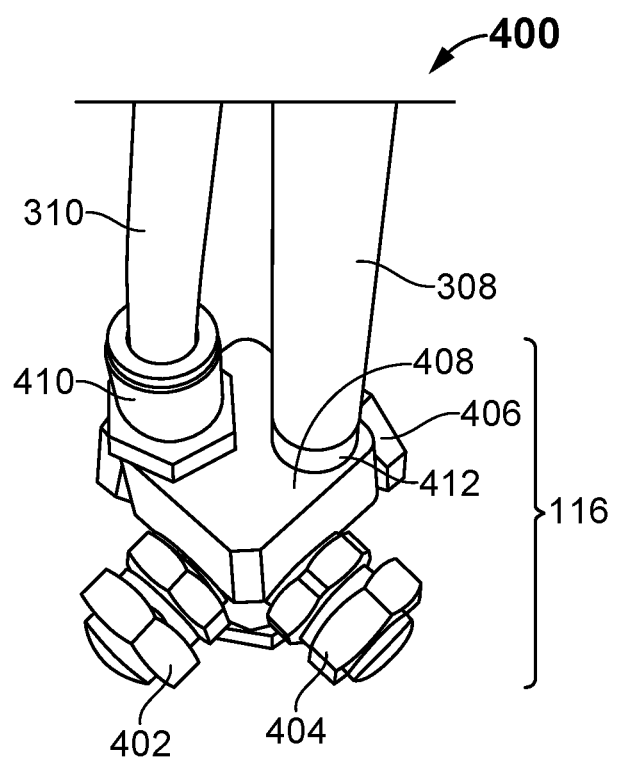
FIG. 4 illustrates an enlarged view of a spray nozzle in one embodiment of the present invention.

Referring now to FIG. 4, an enlarged view 400 of the spray nozzle 116 is shown. In one embodiment, the spray nozzle 116 comprises one or more sprayers and a hollow spray housing 408. The one or more sprayers include, but not limited to, a first sprayer 402, a second sprayer 404, and a third sprayer 406 (fourth sprayer not shown). The sprayers (402, 404, and 406) are mounted at the outer periphery of the hollow spray housing 408. The spray nozzle 116 is in communication with the solution chamber 118 and the pressure gauge 304 using the sanitization solution feed hoses (302 and 310) and the nitrogen tube feed conduit 308. The sanitizing feed hose lower end 310 and the nitrogen tube feed conduit 308 are connected to the hollow spray housing 408 of the spray nozzle 116. In one embodiment, the sanitizing feed hose lower end 310 is connected to the hollow spray housing 408 using a connector 410. The nitrogen tube feed conduit 308 is connected to the hollow spray housing 408 using a connection point 412 that is able to withstand the pressures, for example, 10-60 PSI but may be higher depending upon the size of the tank to be sanitized (e.g., 60-200 PSI). The spray nozzle 116 receives a defined amount of nitrogen at pressure, for example, 60 PSI, through the nitrogen tube feed conduit 308 and sanitizing agent through the sanitizing feed hose lower end 310. The nitrogen and the sanitizing agent are mixed together at the hollow spray housing 408. In one embodiment, the spray nozzle 116 may comprise a cylinder for automatic operation, clean-out and/or shut-off needles, may be siphon or gravity-fed configurations, internal or external mixes, and may be variable in nature so as to provide independent control of liquid, atomizing nitrogen and fan nitrogen pressure for fine tuning of flow rate, drop size, spray distribution and coverage. In one embodiment, the spray nozzle 116 comprises one or more clean-out and/or shut-off needles, and an anti-bearding nitrogen caps that resist build-up around the nozzle orifice.

Figure 5:
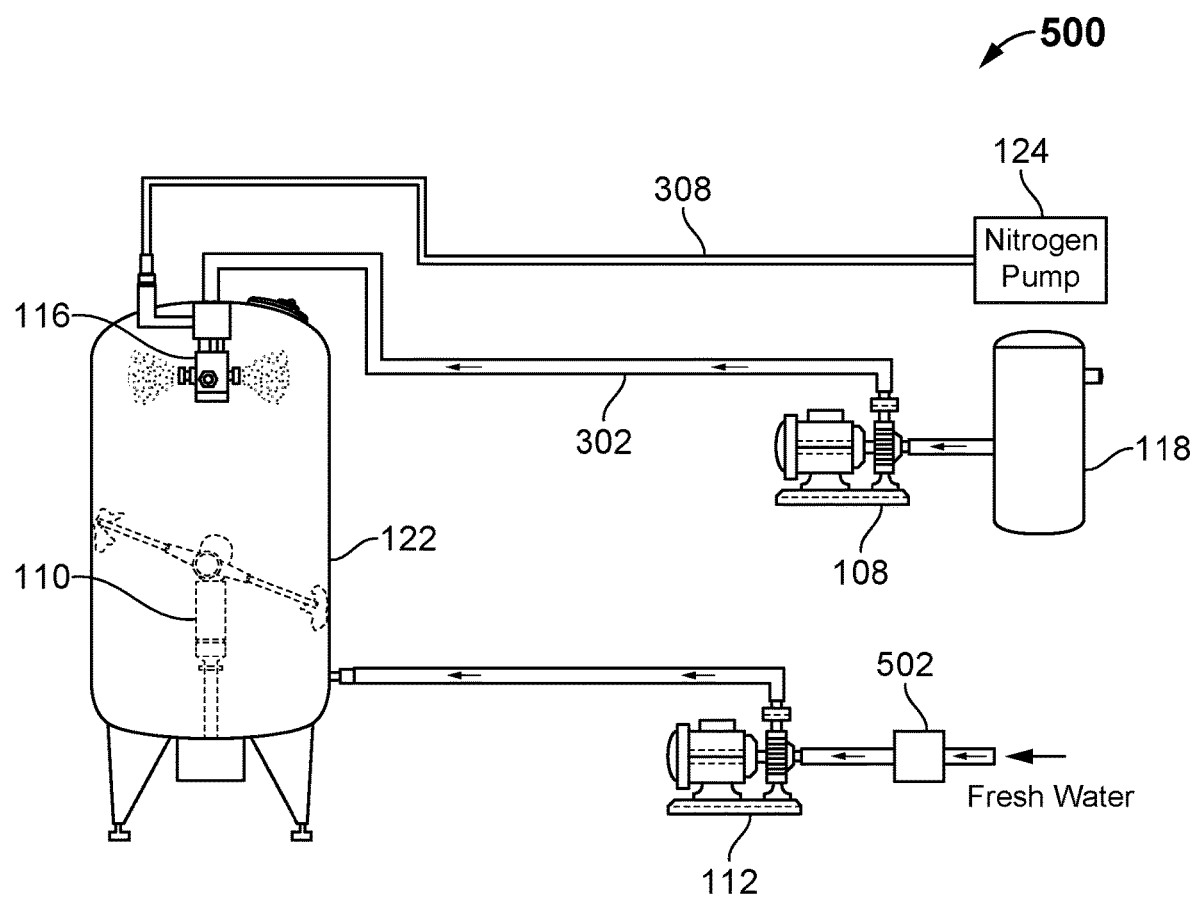
FIG. 5 illustrates an arrangement for cleaning, rinsing, and sanitizing the container using the system in another embodiment of the present invention.

Referring now to FIG. 5, an arrangement 500 for cleaning, rinsing, and sanitizing the container 122, for example, a winery tank in another embodiment of the present invention is disclosed. In one embodiment, the spray nozzle 116 is disposed within the container 122 at the top portion and the CIP device 110 is disposed at the bottom portion within the container 122. In one embodiment, the solution chamber 118 is fluidly connected to the spray nozzle 116 via a sanitization feed hose 302 for circulating the liquid solution, for example, a sanitizing agent, using at least one pump 108. In one embodiment, a nitrogen pump 124 is used for supplying nitrogen from outside environment to the container 122 via a nitrogen tube feed conduit 308. The spray nozzle 116 facilitates to dispersion of the liquid solution with the nitrogen into a mist/spray for effectively sanitizing the container 122. In one embodiment, the liquid solution, for example, water, is circulated to the container 122 using at least one pump 112 for cleaning and rinsing the container 122 using at least one CIP device 110, for example, a spray ball. In one embodiment, at least one volumetric meter 502 is connected to an inlet of the liquid solution for measuring the volume or flow rate of the liquid solution that is passing through a conduit in a set period of time.

Figure 6:
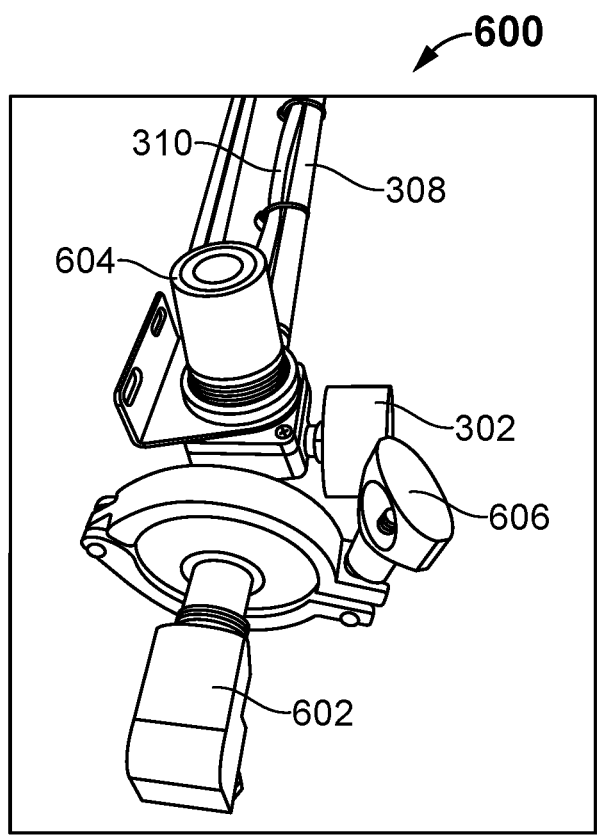
FIG. 6 illustrates an enlarged side perspective view of a pressure gauge connected to an nitrogen intake pipe in one embodiment of the present invention.
Figure 7:
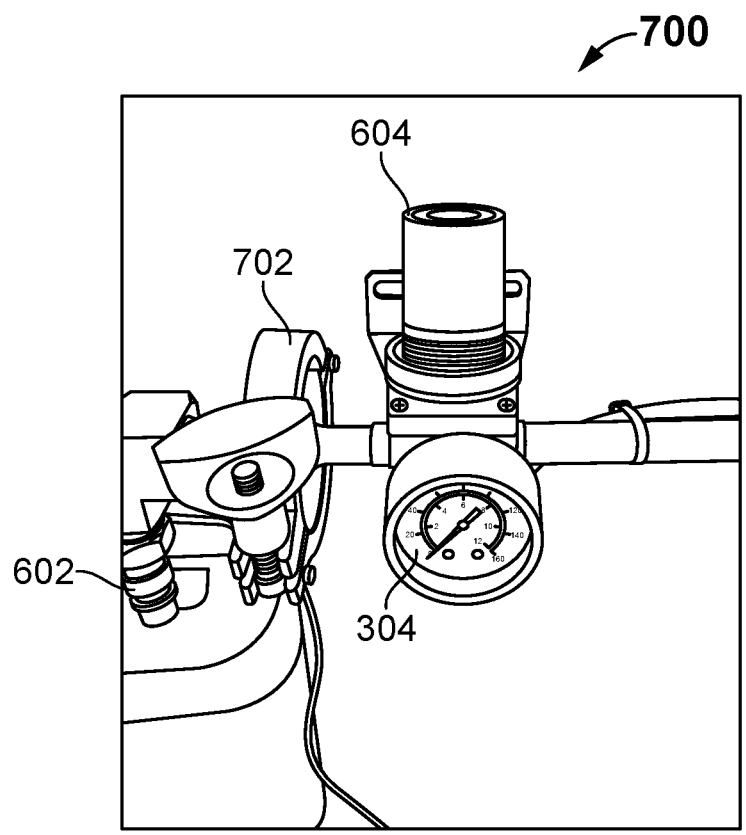
FIG. 7 illustrates an enlarged top perspective view of the pressure gauge connected to the nitrogen intake pipe in one embodiment of the present invention.

Referring now to FIGS. 6 and 7, an enlarged view of the pressure gauge 304 connected to a nitrogen intake pipe 602 from an nitrogen pump is shown. FIG. 6 illustrates an enlarged side perspective view 600 of the pressure gauge 304. FIG. 7 illustrates an enlarged front perspective view 700 of the pressure gauge 304. In one embodiment, one or more regulator valve and pressure transducers 604 are installed on the nitrogen intake pipe 602. The valve and pressure transducers 604 are configured to measure the intake nitrogen pressure. In one embodiment, the regulator valve and pressure transducers 604 are configured to regulate the intake nitrogen pressure to the desired pressure range. The intake nitrogen pressure is displayed on the pressure gauge 304. The regulated nitrogen is passed to the spray nozzle 116 through the nitrogen tube feed conduit 308. In addition, the sanitizing agent is also passed to the spray nozzle 116 via the sanitizing feed hose lower end 310. In one embodiment, a pressure safety relief valve 606 is installed to the nitrogen intake pipe 602 via a latch 702. In one embodiment, the pressure safety relief valve 606 controls the upstream pressure of the intake nitrogen by exhausting the over-pressurization to protect the components.

Figure 8:
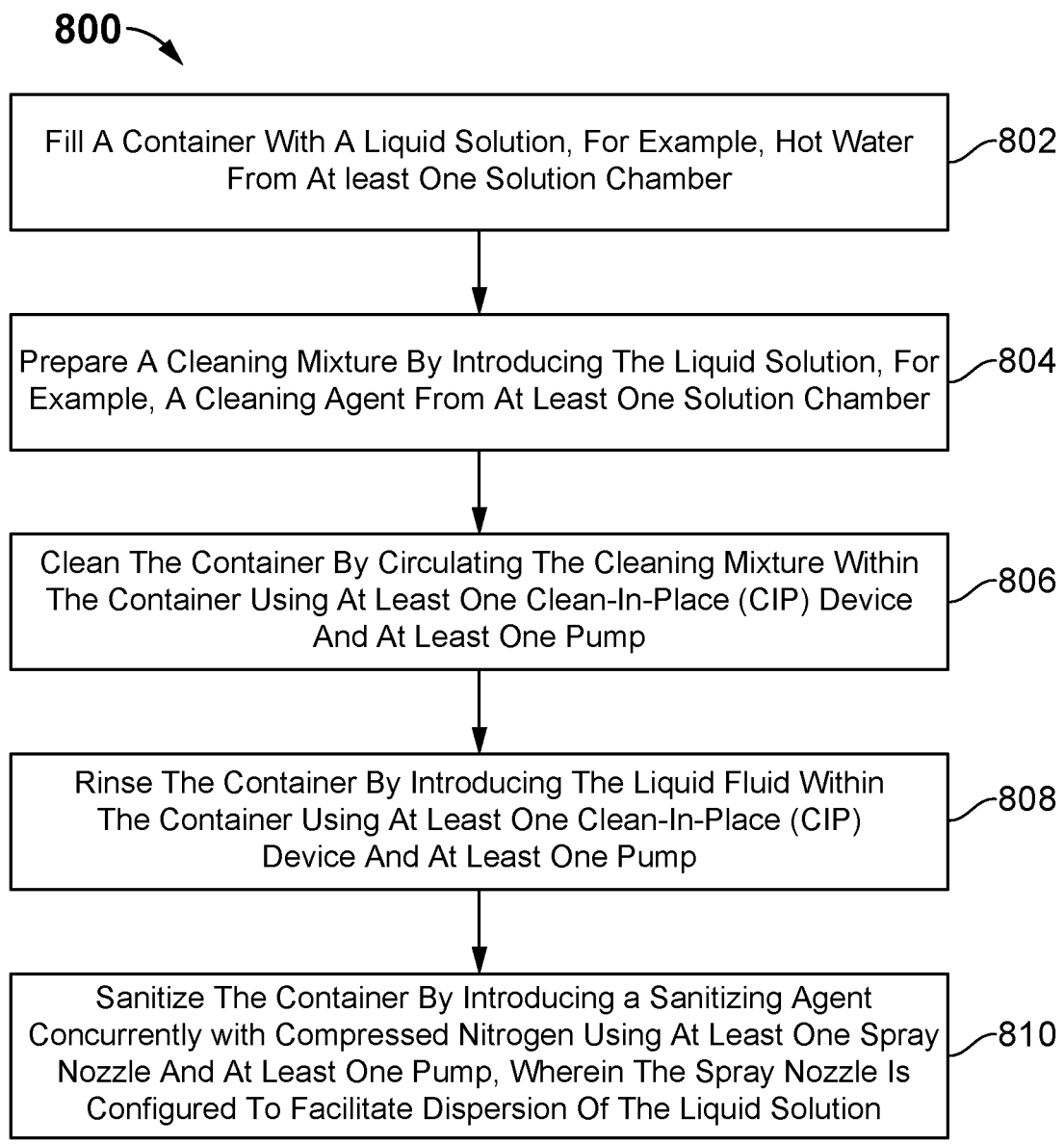
FIG. 8 illustrates a method for cleaning, rinsing, and sanitizing the container using the system in one embodiment of the present invention.

Referring to FIG. 8, a method 800 for cleaning, rinsing, and sanitizing the container 122 using the system 100 in one embodiment of the present invention is disclosed. In embodiments, the tank is 6,000 gallons, but may be any size. In some embodiments, the factors such as volumes, temperatures, and times used in the method 800 may vary based on the specific criteria such as container size. At step 802, the container 122 is filled with a liquid solution, for example, hot water from at least anyone of the solution chamber 104. In one embodiment, the predetermined time for stirring the hot water is approximately, but not limited to, 15-30 minutes. In an exemplary embodiment, the amount of liquid solution ranges from about, but not limited to, 50 to 100 gallons. At step 804, a cleaning mixture is prepared by introducing the liquid solution, for example a cleaning agent from at least one solution chamber 102. In an exemplary embodiment, the amount of liquid solution, for example, cleaning agent ranges from one to four ounces and is mixed with water. Optionally, the cleaning agent is mixed with any one of the liquid solutions, for example, water prior to introducing into the container 122. At step 806, the container 122 is cleaned by circulating the cleaning mixture within the container 122 using at least one CIP device 110, for example, a spray ball, and at least one pump 108. At step 808, the container 122 is rinsed by introducing the liquid fluid, for example, water, from the solution chamber 104 using at least one CIP device 114 and at least one pump 112. In one embodiment, the liquid fluid, for example, water is heated for rinsing process using the heater 120. In one embodiment, the heater 120 is fluidly connected to the solution chamber 104 via a conduit. Further, at step 810, the container 122 is sanitized by introducing a sanitizing agent, for example PAA within the container 122 using at least one spray nozzle 116 and at least one nitrogen pump 124 such that the sanitizing agent and nitrogen are mixed at the spray nozzle under pressure, for example, 10-60 PSI. The spray nozzle 116 is configured to facilitate dispersion of the liquid fluid via nitrogen pump, for efficiently sanitizing the container 122. In one embodiment, the sanitizing agent is, but not limited to, a chlorine dioxide ($ClO_2$) or a peracetic acid (PAA). In one embodiment, amount of sanitizer is 0.5 gallons. Then, the container 122 is sealed for at least, but not limited to, 15 minutes and then unsealed or exposed to sanitizing agent and nitrogen mix to dry naturally. In operation, the system and method described herein uses 100-200 gallons of fresh water, whereas known wine tank cleaning systems and methods use between 400-500 gallons of fresh water. In the sanitization step, water use is only 0.5 gallons compared to 150 gallons with traditional methods.

Referring to FIG. 9, a table 900 displays test results according to one embodiment of the present invention is disclosed. In one embodiment, the test results describe comparative efficacy study of chlorine dioxide/nitrogen spray versus chlorine dioxide rinse, which are used for cleaning different tanks, for example, at least six tanks. In one embodiment, the tanks are indicated with a number, for example, 814, 13, 11, 10, 9, and 5. The tanks have storage capacity ranges from about, but not limited to, 6075-6113 gallons. The tanks are used to store different type of wines such as, but not limited to, cabernet sauvignon, chardonnay, sauvignon blanc, and merlot. The study methodology was as follows: first the tanks were emptied and rinsed with warm water and pre-treatment microbiological swab samples were collected from the floor, wall, ceiling, and rack port/valve of each tank. In one embodiment, the tanks are cleaned with 270 XTRA and citric acid and then post cleaning microbiological swab samples were collected from each tank.

In one embodiment, three tanks 814, 13, and 11 were sanitized with chlorine dioxide and nitrogen spray and other tanks 10, 9, and 5 were sanitized with chlorine dioxide rinse. The post-sanitizer microbiological swab samples were collected from each tank. Further, the microbiological swab samples were processed at the laboratory; and the survivability, percent colony forming units (CFU) reduction, and Log 10 CFU reduction of microbe populations after cleaning and after sanitizing steps was determined and compared.

In one embodiment, the post cleaner (CFU) value of the microbial load on the rack port of the tank 814 is 332 and the post sanitizer (CFU) value of the microbial load on the rack port/valve is 21. The chlorine dioxide/nitrogen spray was significantly more effective at reducing microbial populations on the rack port/valve of the tank 814. When comparing the performance of the chlorine dioxide/nitrogen spray (applied to the tanks 814, 13, and 11) to the chlorine dioxide rinse (applied to the tanks 10, 9, and 5), the chlorine dioxide/nitrogen spray was significantly more effective at reducing microbial populations on the tank 814 surfaces sampled: floor, wall, ceiling, and rack port/valve.

The post cleaner (CFU) value of the microbial load on the rack port/valve of the tank 13 is 32 and the post sanitizer (CFU) of the microbial load on the rack port/valve is 0. The chlorine dioxide/nitrogen spray was significantly more effective at reducing microbial populations on the rack port/valve, floor, wall, and the ceiling of the tank 13.

In one embodiment, the post cleaner (CFU) value of the microbial load on the rack port/valve of the tank 11 is 37 and the post sanitizer (CFU) of the microbial load on the rack port/valve is 4. The chlorine dioxide/nitrogen spray was significantly more effective at reducing microbial populations on the rack port/valve, floor, wall, and the ceiling of the tank 11.

The post sanitizer (CFU) values of the microbial load on the floor, wall, ceiling, and the rack port of the tank 10 are 18, 12, 13, and 16, respectively. The chlorine dioxide rinse is used for cleaning the tank 10. The chlorine dioxide rinse was significantly less effective at reducing microbial populations on the rack port/valve, floor, wall, and the ceiling of the tank 10.

The post sanitizer (CFU) values of the microbial load on the wall and the rack port of the tank 9 are 10 and 12, respectively. The chlorine dioxide rinse is used for cleaning the tank 9. The chlorine dioxide rinse was significantly less effective at reducing microbial populations on the wall and the rack port of the tank 9.

The post sanitizer (CFU) values of the microbial load on the ceiling and the rack port of the tank 5 are 11 and 97, respectively. The chlorine dioxide rinse is used for cleaning the tank 5. The chlorine dioxide rinse was significantly less effective at reducing microbial populations on the ceiling and the rack port of the tank 5.

The results showed the following: The cleaning step with 270 XTRA/citric acid significantly reduced microbial populations at all swab sites sampled on all six tanks compared to the pre-treatment samples. When compared to the post-cleaner results, both sanitizers (chlorine dioxide/nitrogen spray and chlorine dioxide rinse) further significantly reduced microbial loads on the floor, wall, ceiling, and rack port/valve of all six tanks. When comparing the performance of the chlorine dioxide/nitrogen spray (applied to Tanks 814, 13, and 11) to the chlorine dioxide rinse (applied to Tanks 10, 9, and 5), the chlorine dioxide/nitrogen spray was significantly more effective at reducing microbial populations on all tank surfaces sampled: floor, wall, ceiling, and rack port/valve. The superior performance of the chlorine dioxide/nitrogen spray compared to the chlorine dioxide rinse was reflected in survivability of microbe populations, the average percent CFU reduction, and the average Log 10 reduction.

Referring to FIG. 10, a table 1000 displays test results according to one embodiment of the present invention is disclosed. In one embodiment, the test results describe comparative efficacy study of chlorine dioxide mist versus peracetic acid rinse on interior surfaces of stainless-steel tanks. In one embodiment, the tanks are indicated with a number, for example, 231, 206, 209, 234, 216, and 214. The tanks 231, 206, 209, 234, 216, and 214 have storage capacity ranges from about, but not limited to, 6259-15091 gallons. From FIG. 10, it is evidence that the system uses only 0.5 g of sanitizing agent (PAA or $ClO_2$) spray or mist whilst having the same, similar or better effect as the rinse. The study methodology was as follows: first the tanks were emptied and rinsed with warm water and pre-treatment microbiological swab samples were collected from the floor, wall, ceiling, and rack port/valve of each tank. In one embodiment, each tank is cleaned with 231 XTRA and citric acid and then post cleaning microbiological swab samples were collected from each tank. In one embodiment, three tanks 231, 206, and 209 were sanitized with chlorine dioxide/nitrogen spray or mist and other tanks 234, 216, and 214 were sanitized with peracetic acid rinse. The post sanitizer microbiological swab samples were collected from the floor, wall, ceiling, and rack port/valve of each tank. Further, the microbiological swab samples were processed at the laboratory; and the survivability, percentage of colony forming units (CFU) reduction, and Log 10 CFU reduction of microbe populations after cleaning and after sanitizing steps was determined and compared. When comparing the performance of the chlorine dioxide/nitrogen spray (applied to Tanks 231, 206, and 209) to the chlorine dioxide rinse (applied to Tanks 234, 216, and 214), the chlorine dioxide/nitrogen spray was significantly more effective at reducing microbial populations on all tank surfaces sampled: floor, wall, ceiling, and rack port/valve.

Preferred embodiments of this invention are described herein, including the best mode known to the inventors for carrying out the invention. It should be understood that the illustrated embodiments are exemplary only and should not be taken as limiting the scope of the invention.

Although specific features of various embodiments of the invention may be shown in some drawings and not in others, this is for convenience only. In accordance with the principles of the invention, the feature(s) of one drawing may be combined with any or all of the features in any of the other drawings. The words "including," "comprising," "having," and "with" as used herein are to be interpreted broadly and comprehensively, and are not limited to any physical interconnection. Moreover, any embodiments disclosed herein are not to be interpreted as the only possible embodiments. Rather, modifications and other embodiments are intended to be included within the scope of the appended claims.

I claim:

1. A method for cleaning a foodstuff container, the method comprising the steps of:
   (a) heating water; then
   (b) introducing the heated water to rinse the container; then
   (c) connecting the container to a sanitizing agent chamber; then
   (d) introducing a cleaning agent with a clean-in-place (CIP) device via one or more conduits, wherein cleaning agent is a mixture of caustic cleaner and water to the container; then
   (e) rinsing the container by introducing a second water to rise the container using the at least one (CIP) device and at least one pump; then
   (f) pumping a gas at pressure into a housing of a nozzle concurrently with the sanitizing agent; then
   (g) mixing the gas with the sanitizing agent in the housing; then
   (h) pressurizing the gas and sanitizing agent mixture in the housing; then
   (i) dispersing the sanitizing agent and gas mixture to form a mist of sanitizing agent and gas into the container for sanitizing the container.

2. The method of claim 1, wherein the gas is Nitrogen.

3. The method of claim 1, further comprises connecting a nitrogen source to a nitrogen pump and the spray nozzle via a conduit, and supplying the nitrogen from the nitrogen source to the spray nozzle at pressure, and dispersing the sanitizing agent nitrogen mixture as a spray for sanitizing the container.

4. The method of claim 1, wherein the pressure is 10-60 PSI.

5. The method of claim 1, wherein the sanitizing agent is at least any one of a chlorine dioxide ($ClO_2$) and a peracetic acid (PAA).

6. The method of claim 1, wherein the container is at least any one of a wine tank or a beer tank or barrel, and spirit storage tank.

7. The method of claim 1, further comprising draining the water from the container and recovering the water using a valve at a bottom portion of the container, wherein the water is rinse liquid.

* * * * *